United States Patent [19]
Proulx et al.

[11] Patent Number: 5,477,155
[45] Date of Patent: Dec. 19, 1995

[54] CURRENT FLOW INTEGRITY TEST

[75] Inventors: Stephen Proulx, Littleton; John L. Burns, Jr., Dracut; Scott Emory, Boston; Richard W. Gray, Chestnut Hill; Frank M. Lentine, Bedford, all of Mass.

[73] Assignee: Millipore Corporation, Bedford, Mass.

[21] Appl. No.: 105,525

[22] Filed: Aug. 11, 1993

[51] Int. Cl.⁶ .................................................. G01N 27/02
[52] U.S. Cl. ........................................ 324/71.1; 324/439
[58] Field of Search ................................ 324/376, 71.1, 324/425, 439, 639, 557

[56] References Cited

U.S. PATENT DOCUMENTS

| | | | |
|---|---|---|---|
| 2,821,680 | 1/1958 | Slusser | 324/376 |
| 3,617,868 | 11/1971 | Beitel | 324/376 |
| 4,211,106 | 7/1980 | Swanson | 73/38 |
| 4,628,267 | 12/1986 | Lee | 324/376 |
| 4,644,283 | 2/1987 | Vinegar | 324/376 |
| 4,734,649 | 3/1988 | Barnaby | 324/376 |
| 4,924,187 | 5/1990 | Sprunt et al. | 324/376 |
| 4,926,128 | 5/1990 | Givens | 324/376 |
| 5,183,545 | 2/1993 | Branca et al. | 204/252 |

*Primary Examiner*—Maura K. Regan
*Attorney, Agent, or Firm*—Andrew T. Karnakis; Paul J. Cook

[57] ABSTRACT

A new method and apparatus is described for conducting an integrity test on porous membranes and membrane filters and for conducting a pore-size characterization of membrane. The method and apparatus apply to membrane integrity tests and pore-size characterizations which are based on the dependence on the pore size of the pressure required to intrude a non-wetting, electrically conductive liquid into and through the pores. Electrical-measurement methods are described for identifying the pressure at which intrusion occurs.

48 Claims, 3 Drawing Sheets

CURRENT FLOW INTEGRITY TEST

BACKGROUND OF THE INVENTION

This invention relates to a method and apparatus for determining both the pore-size characteristics and integrity of porous membranes and membrane filters and employs miscible liquids, at least one of which is electrically conductive, which do not spontaneously wet the porous structure of the membrane. Specifically, this invention relates to a method and apparatus for determining the pore-size characteristics and/or integrity of a membrane or filter based upon the use of electrically conductive liquids and electrical measurements.

Presently, the pore-size characterization and determination of integrity for membranes and filters, in general, are performed via procedures which are referred to as, among other things, "air-flow porosimetry", the "bubble-point test" or "bubble-point determination", and the "diffusion test". In addition, hydrophobic membranes, specifically, can also be characterized and tested by procedures referred to as, among other things, the "water intrusion-pressure determination" and the "water-flow test" or "water-intrusion test".

The bubble-point test and air-flow porosimetry utilize a liquid which spontaneously wets the membrane in question, and are based on the fact that subsequent attempts to displace the wetting liquid with a gas require that the gas pressure be elevated to some critical level dependent on the size of the pores, or the size of defects if present, in order to overcome the surface-tension forces holding the liquid in the pores. The equation for this critical pressure, defined as the bubble-point pressure, is a variation of the Young-Laplace equation for capillary pressure drop, in this application often called the Washburn equation:

$$P_{BUBBLE\ POINT} = 4K\sigma \cos(\theta)/d \qquad (Eqn.\ 1)$$

where $P_{BUBBLE\ POINT}$=bubble-point pressure
K=the pore perimeter (shape) correction factor
σ=surface tension of the liquid
θ=contact angle of the liquid against the solid
d=the diameter of the pore Equation 1 is rarely actually used to quantitatively calculate a pore size from empirical bubble-point data, since the pore perimeter correction factor, K, is rarely known independently. Instead, since the equation indicates that the bubble point is inversely related to the pore diameter, it is used as a justification to qualitatively rank the relative pore size of membranes according to their bubble-point pressures. Further, since particle retention efficiency is related to the pore size, Equation 1 also serves as a conceptual justification for empirically correlating the retention efficiency of membranes of various pore sizes to their bubble points. Membrane manufacturers have taken advantage of this retention-vs.-bubble-point relationship to identify the critical bubble point required for a desired level of retention, and filter users conduct bubble-point determinations to confirm that the filter in question is integral and of the appropriate pore size.

Air-flow porosimetry and a visual version of the bubble-point test for membrane samples are described by ASTM Method F316-86. In general, the bubble-point test is performed by prewetting the membrane with the liquid to be used and mounting the membrane in a specially designed holder which allows a visually observable layer of liquid to be placed on the downstream, i.e. upper side of the membrane. In the case of a bubble-point test of an enclosed filter, the filter is flushed with the liquid to wet the membrane. The pressure of air or other gas on the upstream side of the membrane is then increased, and the downstream liquid layer or the outlet from the enclosed filter is observed for the formation of continuous streams of bubbles. The pressure at which these first appear is called the bubble-point pressure of the sample.

For relatively large filters, which experience significant diffusion rates at pressures below the bubble point as discussed below, a more analytical method is used to determine the bubble-point pressure. In this case, the rate of flow of gas through the filter is measured as a function of the imposed gas pressure, and the pressure at which the flow makes a transition from relatively low flow rates, which is indicative of diffusion only to significantly higher flow rates, which is indicative of bulk gas flow through pores or defects is referred to as the bubble-point pressure of the filter.

Porosimetry is used to determine the relative pore-size distribution of a membrane or membrane filter. In this procedure, the flow rate of gas through a pre-wetted membrane at a particular gas pressure is divided by the flow rate of gas through an initially dry identical membrane at the same pressure. The resulting mathematical ratio, R, is plotted as a function of imposed pressure, and the first derivative of this function, dR/dP, yields a bubble-point pressure distribution, which, via the bubble-point equation shown above, also indicates the relative distribution of pore sizes, as well.

The diffusion test is used primarily for relatively large filters and indicates whether or not the filter is integral via a measurement of the gas flow rate through the filter when exposed to a constant upstream gas pressure equal to, or slightly below, the minimum bubble-point pressure required for the filter. Similar to a bubble-point test, the filter is pre-wet with the intended liquid. At a properly selected test pressure, the measured flow rate will be relatively low when the filter is integral and of the appropriate pore size. The source of gas flow through an integral filter at pressures below the actual bubble point of the filter is dissolution of gas into, diffusion through, and re-evaporation from the liquid filling the pores, without forcing the liquid out of the pores. In such a test, a filter with an undesirably large pore size or with a defect will exhibit relatively large gas flow rates as a result of the test pressure being in excess of the filter's actual bubble point.

The water intrusion-pressure determination for hydrophobic filters is conducted via a method similar to the bubble-point determination with the exception that in an intrusion-pressure determination, the membrane is initially dry and the pressure at which water intrudes into and through the membrane is noted. The pressure at which this occurs is, like the bubble-point (Eqn. 1), inversely related to the pore size and is, therefore, justifiably used to indicate the relative pore size of various membranes and can be correlated to retention efficiency:

$$P_{INTRUSION} = -4K\sigma \cos(\theta)/d \qquad (Eqn.\ 2)$$

The negative sign results from the fact that the contact angle of water on a hydrophobic solid is greater than 90 and thus the cosine is negative.

The water-flow test, like the diffusion test, is conducted at a constant pressure. In this case, the upstream side of a dry hydrophobic filter is exposed to water at a constant pressure equal to, or slightly below, the minimum intrusion pressure required for the filter, and a measurement of the water flow rate into the filter's housing is made. This measurement is conveniently performed on the upstream side of the filter, either by measuring the flow of water directly with a flow meter, or by measuring the pressure as a function of time in an adjoining gas space and calculating the gas expansion rate, which just equals the water flow rate. The latter is presently performed by automated testing devices. However, it is also possible to measure the downstream gas flow rate and equate this to the upstream water flow rate since the upstream water, membrane, and downstream air all move approximately together in a piston-like fashion at pressures below the intrusion pressure of the membrane.

Unlike the diffusion test, the relatively low water flow rates observed in a water-flow test conducted at a pressure below the normal water intrusion pressure are not due to gas diffusion. Instead, the water flow results from water flowing forward to fill the volume vacated by the shifting, compaction, and stretching of a pleated membrane structure common to many large-area filters. In an actual water-flow test, an observed low flow rate is indicative of pleat compaction only, and thus of an integral filter, and a large flow rate is indicative of water flowing through undesirably large pores or a defect which is successfully intruded at the test pressure.

The water intrusion-pressure determination and the water-flow tests offer an important advantage for hydrophobic filters as compared to a bubble-point determination and diffusion test: the latter two require the use of a low-surface-tension liquid, e.g. an alcohol or an alcohol-water mixture, to initially wet the hydrophobic filter, and the use of such liquids pose safety and disposal problems that do not exist for the water-flow test nor the water intrusion-pressure determination.

In spite of the above stated advantage of the water intrusion-pressure determination and the water-flow test, an additional feature is desirable for these tests. As mentioned above in the case of a pleated filter construction, the water flow into the housing experienced by a filter exposed to a pressure below the water intrusion pressure is due to the compaction of the pleated-membrane structure, which in no way is related to the pore size or the pore-size distribution of the membrane. Therefore, it is desirable to use, instead of a water flow-rate measurement, a different measurement which 1. is affected by the membrane or filter only via the pore size,
2. results in a smaller range of measured values at imposed pressures less than the intrusion pressure, which in turn
3. makes changes in the measured value more obvious as the imposed pressure is taken through the range over which the various sizes of pores are intruded, resulting in a more precise description of the relative pore-size distribution, and
4. makes at a single pressure below the required intrusion pressure, the measured value for a defective filter more obviously different from those for normal integral filters.

SUMMARY OF THE INVENTION

The present invention is based on the discovery that, with the use of an electrically conductive liquid and an initially dry, electrically nonconductive porous membrane or membrane filter which is not spontaneously wet by the electrically conductive liquid, electrical measurements can be used to identify the pressure at which the liquid intrudes into and through the pores or defects of the membrane, and further that this phenomenon can be used to make more precise determinations of the intrusion pressure and relative pore-size distributions, and more sensitive determinations of whether or not a defect in the membrane exists than could be made via previous methods. Intrusion of the electrically conductive liquid into the membrane changes the electrical conductivity across the membrane. This electrical conductivity change can be measured across the membrane or in a liquid downstream from and in fluid communication with the membrane. Measurement of electrical conductivity change can be made directly or indirectly by effecting an electrical measurement which can be correlated to the electrical conductivity change such as conductance, resistivity, resistance, capacitance, voltage drop, current flow or the like in an electrical circuit which includes the membrane and/or the downstream liquid. The measurement of change in electrical characteristic of the membrane or of the downstream liquid, directly or indirectly provides an accurate means for measuring intrusion of the electrically conductive liquid into the membrane as a function of pressure changes and therefore an accurate means for measuring porosity characteristics of the membrane.

In one embodiment of this invention, an electrical measurement is made directly or indirectly across the membrane. At least one surface of the membrane is exposed to a pressurized electrically conductive liquid. The electrically conductive liquid comprises a composition which does not intrude the membrane in the absence of a pressure differential across the membrane. This embodiment is particularly useful for determining relative pore size characteristics of the membrane such as bubble point, porosity or the like.

In a second embodiment, an electrical measurement is made directly or indirectly within a liquid ("downstream" liquid) in contact with the membrane at a pressure less than the pressure of the upstream pressurized electrically conductive liquid. The pressurized liquid flows from an "upstream" surface of the membrane through the membrane and into the "downstream" liquid.

The process of this invention relies on the fact that as the upstream pressure is increased and electrically conductive liquid intrusion begins to take place, the intruding liquid changes the electrical conductivity across, the membrane and mixes with the downstream liquid, thereby changing the electrical conductivity (and resistivity) within the membrane and of the downstream liquid.

When utilizing both embodiments, pressure of the "upstream" liquid can be maintained below the pressure at which intrusion would occur in a defect free membrane. Should intrusion be detected under these conditions, the membrane is deemed to contain defects due to openings in the membrane which permit liquid intrusion. Alternatively, the transmembrane pressure can be maintained to include a pressure range above the normal intrusion pressure. Under these pressure conditions, the relative pore size characteristics of the membrane can be determined since change of electrical conductivity across the membrane can be correlated with pressure which, in turn, can be correlated to membrane pore size characteristics.

When water, and/or a water-salt solution, is used as the electrically conductive liquid, any embodiment of this invention can be used to determine the water intrusion pressure of a membrane or filter, conduct a water-flow test, or obtain an intrusion pressure relative pore-size distribution. A significant feature of this invention is that it offers an extreme measured value e.g. very low transmembrane conductivity, and an extremely small range of values, for integral filters of the proper pore size exposed to pressures below the intrusion pressure of the membrane. This feature permits the identification of defects and undesirably large pores more obvious than via presently available methods, thus making the electrically based tests more sensitive. Further, these electrical methods are based on phenomena which are not dependent on membrane or filter parameters unrelated to pore size such as the filter membrane area, which does affect the results of a diffusion test and membrane flexibility which does affect the result of a water flow rate measurement version of a water-flow test.

DESCRIPTION OF SPECIFIC EMBODIMENTS

Figure 1:
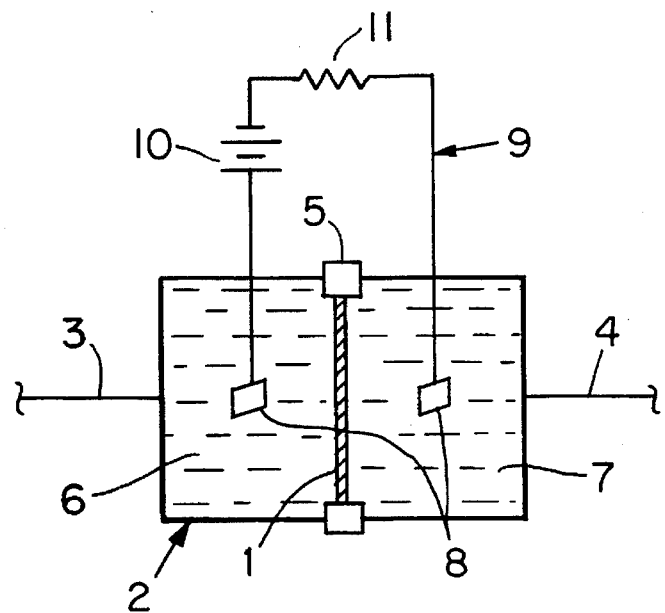
FIG. 1 is a schematic view of an apparatus of this invention wherein transmembrane conductivity is measured.

In accordance with this invention, the porosity characteristics of an electrically nonconducting membrane are determined by electrical means and by employing an electrically conducting liquid which does not wet the membrane structure. This invention is based upon the discovery that membrane porosity characteristics can be determined accurately by rendering the porous pathways through a membrane electrically conductive with an electrically conductive liquid. The liquid must be a nonwetting liquid for the membrane structure being tested so that liquid intrusion into the membrane can be effected only by applying a differential transmembrane pressure such as by applying superatmospheric pressure to the upstream liquid rather than by capillary action or other phenomenon which occurs at atmospheric pressure. The differential transmembrane pressure is required in order to provide a factor which depends upon membrane pore size and which can be measured easily. An electrical circuit including an electrical pathway through the membrane is formed when the pressurized conducting liquid intrudes throughout the thickness of the membrane. The larger pores in the membrane become filled with liquid first and a corresponding electrical characteristic of the circuit is measured. As pressure on the intruding liquid increases, more pores become filled with the liquid and the membrane becomes more electrically conductive. By measuring the pressure-dependent electrical conductivity of the membrane, the porosity characteristics of the membrane can be determined including relative pore size, relative pore size distribution, and membrane integrity.

The electrical measurement can be effected across the membrane and can be effected directly or indirectly such as by utilizing an electrical circuit which includes the membrane, the upstream liquid and the downstream liquid. The electrical measurement made can be a conductivity measurement or one that can be correlated to conductivity including conductance, resistivity, resistance, capacitance, voltage drop or current flow.

Alternatively, the electrical measurement can be effected in the downstream liquid having an initial electrical conductivity different from the conductivity of the upstream liquid. As the upstream liquid passes through the membrane, the electrical conductivity of the downstream liquid changes over time.

When utilizing this either embodiment of this invention, the apparatus can be used to test for defects. The upstream pressurized liquid can be maintained at a pressure below the known intrusion pressure of the membrane. When infiltration of the upstream liquid into the downstream liquid is detected by the change in electrical conductivity of the downstream liquid, the membrane is considered to have defects. The intrusion pressure can be determined by any conventional means such as is described with reference to FIG. 3.

It is to be understood that upstream and downstream electrically conductive liquids which do not wet the membrane structure both can be pressurized to effect infiltration into the membrane in order to increase electrical conductivity of the membrane. Such a procedure can be utilized to determine porosity characteristics of the membrane or to identify the presence of defects in the membrane. This process can be utilized when the pores of the membrane are occupied initially with a gas rather than a liquid.

It is also to be understood a membrane structure tested in accordance with this invention can comprise a membrane having pores occupied initially with a liquid which is immiscible with the downstream and upstream liquid and which is not electrically conductive. The pressurized upstream electrically conductive liquid displaces the liquid within the pores and thereby changes the electrical conductivity of the membrane structure so that the membrane can be tested as in the manner set forth above. A suitable liquid for initially occupying the pores of the membrane is polyethylene glycol utilized in conjunction with an upstream aqueous salt solution such as aqueous ammonium sulfate.

In any embodiment, a plurality of electrodes can be utilized upstream and/or downstream of the membrane to determine defects or pore size characteristics in different areas of the membrane. Alternatively, a single set of electrodes which are movable relative to the membrane can be utilized to identify defects or pore size characteristics in different areas of the membrane.

It is preferred to utilize an aqueous conductive solution such as filtered tap water or an aqueous salt solution as the intrusion liquid in the process of this invention for convenience.

Representative membranes which can be characterized in accordance with this invention are electrically nonconductive microporous or ultrafiltration membranes including those formed from hydrophobic polymers including polyolefins such as polyethylene or polypropylene; polysulfones such as polysulfone or polyethersulfone; fluoropolymers such as polyvinylidene fluoride, polytetrafluoroethylene, or the like. These membranes are not wet by the aqueous intrusion liquid and do not contain water miscible agents such as glycerine or the like.

Electrically nonconductive hydrophilic membranes also can be tested in accordance with this invention. The pores of the hydrophilic membrane can be filled with a third liquid which is immiscible with the downstream liquid and the upstream liquid. Representative suitable hydrophilic membranes include polyamides, e.g. Nylon 66, cellulose, cellulose acetate or the like. Alternatively, the pores of the hydrophilic membrane can be filled with a gas. In this embodiment, liquids which do not wet the membrane are utilized. Nonwetting upstream and downstream liquids which can be utilized include organic liquids made conductive by adding inorganic salts or organic salts, or aqueous liquids which contain sufficiently high concentrations of inorganic salts to prevent the resultant solution from wetting the membrane.

Referring to FIG. 1, wherein like elements to the elements shown in FIG. 1 are identified by the same reference numerals, the two electrical probes 8 are positioned one in each of the upstream liquid 6 and in the downstream liquid 7. An electrical measurement (conductivity, conductance, resistivity, resistance, etc.) between the two probes 8 can be measured directly. Optionally, an electrical circuit 9 containing an appropriately selected voltage source 10 and resistor 11 can be attached to the probes 8; an electrical measurement (conductivity, conductance, resistivity, resistance, capacitance, voltage drop, current flow, etc.) can be measured between any two points in the circuit 9; and the conductivity (etc.) between the two probes calculated with an appropriate electrical-circuit equation. Alternatively, the measurement at an alternate point in the electrical circuit 9 can be used without further calculation to characterize the system.

The relative pore size of a membrane or filter is identified, via an identification of the intrusion pressure of the membrane or filter, by noting the upstream pressure at which, for example, the rate of change of the directly measured conductivity between the probes with respect to increases in pressure increases from a near-zero value (at low pressures) to a significantly larger rate of change. Alternatively, the intrusion pressure can be identified by noting the pressure at which the measured electrical value crosses some predetermined threshold value.

In the apparatus shown in FIG. 1, the applied pressure can be a differential pressure between the two liquids 6 and 7, or both sides of the membrane, can be pressurized identically. The pertinent pressure is then the differential pressure between the liquids 6 and 7 and that of the gas or liquid inside the membrane 1.

The relative pore-size distribution for a sample can be determined by noting the pressures at which, and the total range of pressures over which, changes in the measured electrical value take place with respect to increases in pressure. Changes in the measured electrical value which begin at relatively low pressures indicate that the largest pores are relatively large, while changes that begin at relatively high pressures indicate that the largest pores are relatively small. Changes which continue to take place over a wide range of pressures before returning to near zero indicate that the pore-size distribution is relatively wide, while those which are confined to relatively narrow distributions indicate that the pore-size distribution is narrow.

Figure 2:
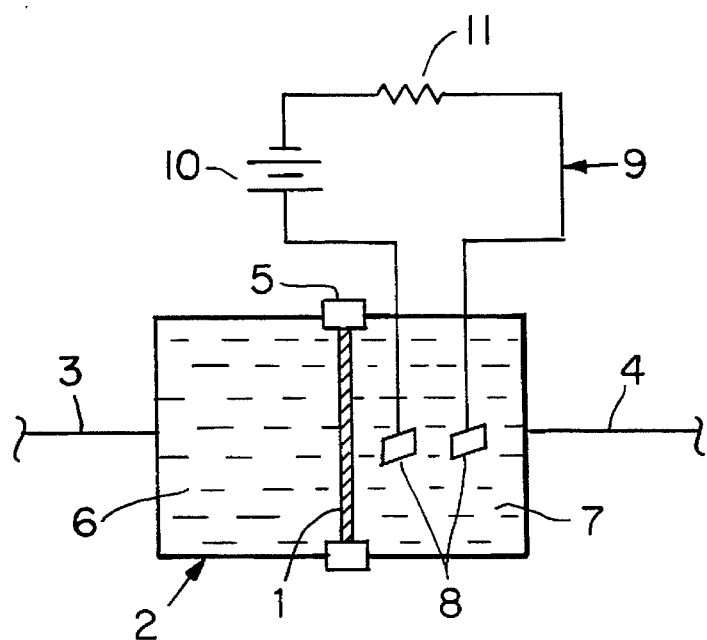
FIG. 2 is a schematic view of an apparatus of this invention wherein downstream liquid conductivity is measured.

Referring to FIGS. 2, a dry, electrically nonconductive, porous membrane or membrane filter 1 is mounted in a membrane holder or filter housing 2 with an inlet 3, outlet 4, and electrical isolators 5. The insulators 5 are not necessary if the holder or housing is electrically nonconductive. The upstream (pressurized) side of the holder or housing is filled with a non-wetting, electrically conductive liquid or solution 6. In this embodiment of this invention, the downstream (atmospheric pressure) side is filled with a non-wetting, electrically nonconductive liquid 7 or a liquid having a significantly different conductivity than the upstream liquid 6 and which is miscible with the upstream liquid 6. In embodiment shown in FIGS. 2, the two electrical probes 8 are both positioned in the downstream liquid 7 near the membrane 1 or in a remote reservoir 12.

Any of the embodiments of this invention can be used to conduct a precise version of the water-flow integrity test by maintaining the upstream pressure constant at, or slightly below, the required intrusion pressure for the filter. For example, in the embodiment shown in FIG. 1, an alternate method consists of increasing the pressure of both the upstream and downstream liquids 6 and 7 equally in an attempt to intrude the membrane from both sides of the membrane rather than from just one. If, at the test pressure, no defects or undesirably large pores exist, the membrane is not intruded. Consequently, the conductivity (etc.) across the membrane thickness does not change.

The following examples illustrate the present invention and are not intended to limit the same.

EXAMPLE 1

This example was conducted utilizing the apparatus shown in FIG. 1. The membrane was an electrically nonconducting 0.2 micron rated polytetrafluoroethylene (PTFE) membrane having a thickness of 2.0 mils, and a porosity of 85%. The electrically conducting liquid (6) on the upstream side of the membrane and the electrically conducting liquid (7) on the downstream side of the membrane was 120 mho water. The voltage source (10) was 1 volt D.C. and the voltage drop was measured across 3300 ohm resistor (11).

An electrical current flow test was performed on the PTFE sample by the following procedure:

a. Air pressure is applied increasingly to the upstream fluid (6).

b. At various pressures, a voltage drop measurement is taken across resistor 11.

c. The change in voltage drop is plotted vs. the applied pressure (actual differential pressure)

Figure 3:
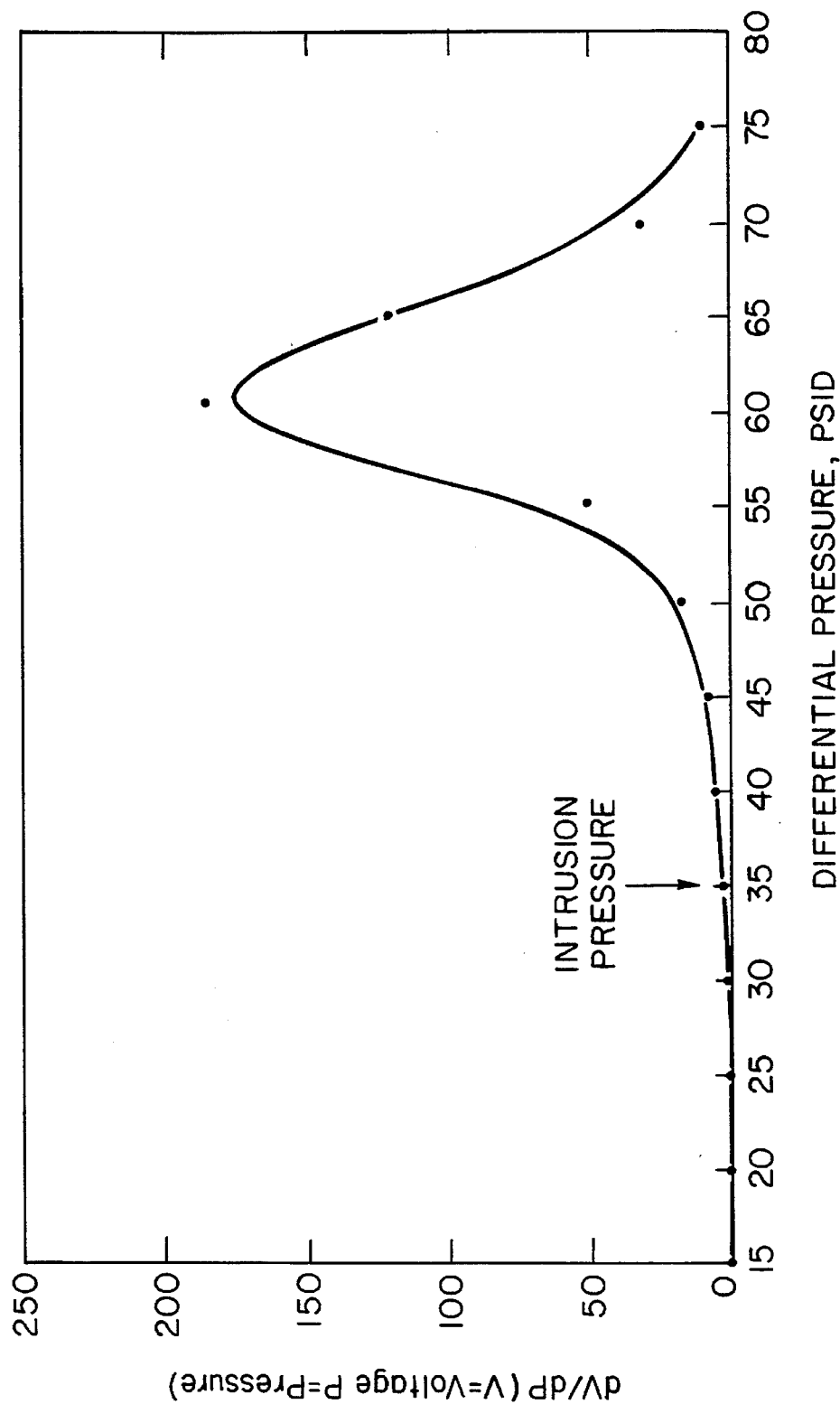
FIG. 3 is a graph showing voltage drop across an external resistor as a function of differential pressure across a membrane.

FIG. 3 represents the intrusion of the water through the membrane sample as measured by voltage drop across the resistor as a function of pressure change. The voltage drop across the resistor increases as the resistance of the membrane decreases due to water intrusion/wetting of the membrane. The intrusion pressure of the membrane is identified when there is an increase in voltage drop from a zero value.

FIG. 3 also represents: the pore size distribution of this membrane sample having a mean intrusion pressure of approximately 60 psid.

Figure 4:
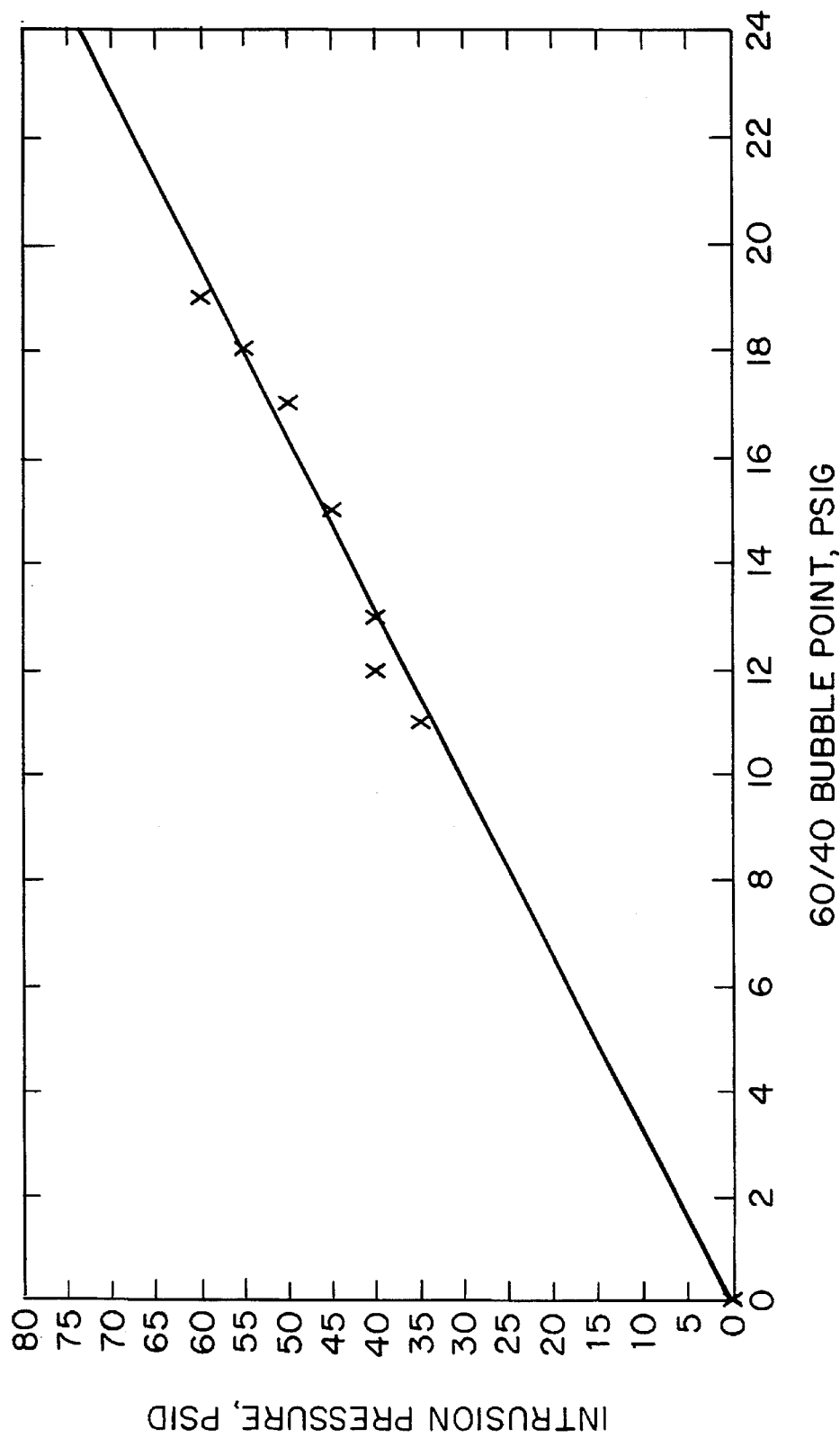
FIG. 4 is a graph of intrusion pressure as a function of bubble point of a membrane.

FIG. 4 represents the relationship of intrusion pressure to bubble point for a plurality of 0.2 micron rated PTFE membranes obtained by the procedure set forth above in this example.

EXAMPLE 2

This example was conducted utilizing the apparatus shown in FIG. 1.

PTFE pleated cartridges manufactured with a bacterial retentive membrane were tested following the same method in example 1 with the exception being a cartridge filter housing was utilized rather than a membrane disc holder. A specific test pressure of 10 psid was utilized. The test pressure of 10 psid is below the intrusion pressure of the membrane. Thus any voltage drop measurements in the electrical current flow test can be attributed to defects.

Table 1 shows both the electrical current flow test values and diffusion test values for a sample of cartridges. These cartridges were then tested for bacterial retention. The results shows the electrical current flow test values can predict retention by the membrane in the cartridge because of the test sensitivity to small defects while the diffusion test cannot. The diffusion test can differentiate large defects only.

TABLE 1

Water Conductivity: 120 mhos
Voltage Drop measured across 3.3K ohm resistor
Voltage supply for circuit: 1 volt DC

| Cartridge Number | Electric Current Flow Test Voltage Drop Across Resistor Microvolts | Bacterial Retentive** | Diffusion Test Value* cc/min |
|---|---|---|---|
| 10 | 7 | Yes | 5.9 |
| 12 | 8 | Yes | 5.5 |
| 4 | 10 | Yes | 7.4 |
| 11 | 12 | Yes | 5.9 |
| 9 | 13 | Yes | 5.9 |
| 6 | 13 | Yes | 6.7 |
| 12 | 14 | Yes | 5.2 |
| 8 | 17 | Yes | 6.1 |
| 17 | 20 | Yes | 5.2 |
| 18 | 26 | Yes | 7.2 |
| 9 | 40 | Yes | 5.5 |
| 27 | 41 | Yes | 5 |
| 4 | 56 | Yes | 6.8 |
| 13 | 78 | Yes | 5.8 |
| 15 | 80 | Yes | 6.7 |
| 3 | 143 | No | 6.7 |
| 48 | 238 | No | 4.4 |
| 46 | 266 | No | 4.9 |
| 14 | 340 | No | 6.4 |
| 41 | 1896 | No | 25.6 |
| 39 | 2260 | No | 25.3 |
| 36 | 3031 | No | 50 |

**Bacterial Retentive: Cartridges challenged following HIMA Guidelines
*Cartridges wet with 60/40 IPA/Water, Nitrogen gas at 10 psig.

We claim:

1. The process for determining porosity characteristic of an electrically nonconductive ultrafiltration or microporous membrane which comprises:

contacting a first surface of said membrane with a second liquid which does not wet said membrane, contacting a second surface of said membrane with a second liquid which does not wet said membrane, increasing pressure on said first liquid to cause said first liquid to intrude said membrane, measuring change in electrical conductivity across said membrane, and correlating said change of electrical conductivity across said membrane with said porosity characteristic.

2. The process of claim 1 wherein said change of electrical conductivity is measured directly.

3. The process of claim 1 wherein said change of electrical conductivity is measured indirectly.

4. The process of any one of claims 1, 2 or 3 wherein said porosity characteristic is intrusion pressure of the membrane.

5. The process of any one of claims 1, 2 or 3 wherein said porosity characteristic is relative pore size of the membrane.

6. The process of any one of claims 1, 2 or 3 wherein said porosity characteristic is bubble point of the membrane.

7. The process of claim 1 wherein a plurality of electrical probes are positioned in said first liquid and said second liquid adjacent opposing surfaces of said membrane.

8. The process of claim 1 wherein a first electrode is positioned in said first liquid and a second electrode is positioned in said second liquid and wherein at least one of said first electrode or said second electrode is movable relative to said membrane.

9. The process for determining a porosity characteristic in an electrically nonconductive ultrafiltration or microporous membrane which comprises:

contacting a first surface of said membrane with an electrically conductive first liquid which does not wet said membrane, contacting a second surface of said membrane with a second liquid which does not wet said membrane, increasing pressure on said first liquid to cause said first liquid to intrude said membrane, measuring change in electrical conductivity of said second liquid, and correlating said change of electrical conductivity in said second liquid with said porosity characteristic.

10. The process of claim 9 wherein said electrical conductivity is measured directly.

11. The process of claim 9 wherein said electrical conductivity is measured indirectly.

12. The process of claim 9 wherein a plurality of electrical probes are positioned in said first liquid and said second liquid adjacent opposing surfaces of said membrane.

13. The process of claim 9 wherein a first electrode is positioned in said first liquid and a second electrode is positioned in said second liquid and wherein at least one of said first electrode or said second electrode is movable relative to said membrane.

14. The process for determining the presence of defects in an electrically nonconductive ultrafiltration or microporous membrane which comprises:

contacting a first surface of said membrane with an electrically conductive first liquid which does not wet said membrane contacting a second surface of said membrane with a second liquid which does not wet said membrane, increasing pressure on said first liquid to a pressure less than a characteristic intrusion pressure of said membrane, and measuring change in electrical conductivity of said second liquid.

15. The process of claim 14 wherein said electrical conductivity is measured directly.

16. The process of claim 14 wherein said electrical conductivity is measured indirectly.

17. The process of claim 14 wherein a plurality of electrical probes are positioned in said first liquid and said second liquid adjacent opposing surfaces of said membrane.

18. The process of claim 14 wherein a first electrode is positioned in said first liquid and a second electrode is positioned in said second liquid and wherein at least one of said first electrode or said second electrode is movable relative to said membrane.

19. The process for determining the presence of defects in an electrically nonconductive ultrafiltration or microporous membrane which comprises:

contacting a first surface of said membrane with an electrically conductive first liquid which does not wet said membrane:

contacting a second surface of said membrane with a second liquid which does not wet said membrane, increasing pressure on said first liquid to a pressure less than a characteristic intrusion pressure of said membrane, and measuring change in electrical conductivity across said membrane.

20. The process of claim 19 wherein said electrical conductivity is measured directly.

21. The process of claim 19 wherein said electrical conductivity is measured indirectly.

22. The process of claim 19 wherein a plurality of electrical probes are positioned in said first liquid and said second liquid adjacent opposing surfaces of said membrane.

23. The process of claim 19 wherein a first electrode is positioned in said first liquid and a second electrode is positioned in said second liquid and wherein at least one of said first electrode or said second electrode movable relative to said membrane.

24. The process for determining a porosity characteristic of an electrically nonconductive ultrafiltration or microporous membrane which comprises:

contacting a first surface of said membrane with an electrically conductive first liquid, contacting a second surface of said membrane with a second liquid, said porous membrane containing a third liquid which prevents said first liquid and said second liquid from wetting said membrane, increasing pressure on said first liquid to cause said first liquid to intrude said membrane, measuring change in electrical conductivity across said membrane, and correlating said change of electrical conductivity across said membrane with said porosity characteristic.

25. The process of claim 24 wherein said change of electrical conductivity is measured directly.

26. The process of claim 24 wherein said change of electrical conductivity is measured indirectly.

27. The process of any one of claims 24, 25 or 26 wherein said porosity characteristic is intrusion pressure of the membrane.

28. The process of any one of claims 24, 25 or 26 wherein said porosity characteristic is relative pore size of the membrane.

29. The process of any one of claims 24, 25 or 26 wherein said porosity characteristic is bubble point of the membrane.

30. The process of claim 24 wherein a plurality of electrical probes are positioned in said first liquid and said second liquid adjacent opposing surfaces of said membrane.

31. The process of claim 24 wherein a first electrode is positioned in said first liquid and a second electrode is positioned in said second liquid and wherein at least one of said first electrode or said second electrode is movable relative to said membrane.

32. The process for determining a porosity characteristic in an electrically nonconductive ultrafiltration or microporous membrane which comprises:

contacting a first surface of said membrane with an electrically conductive first liquid, contacting a second surface of said membrane with a second liquid, said porous membrane containing a third liquid which prevents said first liquid and said second liquid from wetting said membrane, increasing pressure on said first liquid to cause said first liquid to intrude said membrane, measuring change in electrical conductivity of said second liquid, and correlating said change of electrical conductivity in said second liquid with said porosity characteristic.

33. The process of claim 32 wherein said electrical conductivity is measured directly.

34. The process of claim 32 wherein said electrical conductivity is measured indirectly.

35. The process of claim 32 wherein a plurality of electrical probes are positioned in said first liquid and said second liquid adjacent opposing surfaces of said membrane.

36. The process of claim 32 wherein a first electrode is positioned in said first liquid and a second electrode is positioned in said second liquid and said second electrode is movable relative to said membrane.

37. The process for determining the presence of defects in an electrically nonconductive ultrafiltration or microporous membrane which comprises:

contacting a first surface of said membrane with an electrically conductive first liquid, contacting a second surface of said membrane with a second liquid, said porous membrane containing a third liquid which prevents said first liquid and said second liquid from wetting said membrane, increasing pressure on said first liquid to a pressure less than a characteristic intrusion pressure said membrane, and measuring change in electrical conductivity of said second liquid.

38. The process of claim 37 wherein said electrical conductivity is measured directly.

39. The process of claim 37 wherein said electrical conductivity is measured indirectly.

40. The process of claim 37 wherein a plurality of electrical probes are positioned in said first liquid and said second liquid adjacent opposing surfaces of said membrane.

41. The process of claim 37 wherein a first electrode is positioned in said first liquid and a second electrode is positioned in said second liquid and said second electrode is movable relative to said membrane.

42. The process for determining the presence of defects in an electrically nonconductive ultrafiltration or microporous membrane which comprises:

contacting a first surface of said membrane with an electrically conductive first liquid, contacting a second surface of said membrane with a second liquid, said porous membrane containing a third liquid which prevents said first liquid and said second liquid from wetting said membrane, increasing pressure on said first liquid to a pressure less than a characteristic intrusion pressure of said membrane, and measuring change in electrical conductivity across said membrane.

43. The process of claim 42 wherein said electrical conductivity is measured directly.

44. The process of claim 42 wherein said electrical conductivity is measured indirectly.

45. The process of claim 42 wherein a plurality of electrical probes are positioned in said first liquid and said second liquid adjacent opposing surfaces of said membrane.

46. The process of claim 42 wherein a first electrode is positioned in said first liquid and a second electrode is positioned in said second liquid and said second electrode is movable relative to said membrane.

47. The process of any one of claims 24, 32, 37 and 42 wherein said third liquid is polyethylene glycol and said first liquid is an aqueous salt solution.

48. The process of any one of claims 24, 32, 37 and 42 wherein said third liquid is polyethylene glycol and said first liquid is an aqueous solution of ammonium sulfate.

* * * * *